(12) United States Patent
Schwab et al.

(10) Patent No.: US 11,969,493 B2
(45) Date of Patent: *Apr. 30, 2024

(54) OPAQUE COMPOSITION COMPRISING ETHYLENE GLYCOL DISTEARATE

(71) Applicant: Evonik Operations GmbH, Essen (DE)

(72) Inventors: Peter Schwab, Essen (DE); Dominik Schuch, Düsseldorf (DE); Patrick Winter, Mülheim an der Ruhr (DE); Nico Neuhaus, Essen (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/993,428

(22) Filed: Aug. 14, 2020

(65) Prior Publication Data

US 2021/0069077 A1  Mar. 11, 2021

(30) Foreign Application Priority Data

Sep. 5, 2019 (EP) ..................... 19195481

(51) Int. Cl.
| | | |
|---|---|---|
| *A61K 8/37* | (2006.01) | |
| *A61K 8/368* | (2006.01) | |
| *A61K 8/42* | (2006.01) | |
| *A61K 8/46* | (2006.01) | |

(52) U.S. Cl.
CPC .............. *A61K 8/37* (2013.01); *A61K 8/368* (2013.01); *A61K 8/42* (2013.01); *A61K 8/463* (2013.01); *A61K 2800/26* (2013.01); *A61K 2800/30* (2013.01)

(58) Field of Classification Search
CPC . A61K 8/37; A61K 8/368; A61K 8/42; A61K 8/463; A61K 2800/26; A61K 2800/30
See application file for complete search history.

(56) References Cited

U.S. PATENT DOCUMENTS

| | | |
|---|---|---|
| 7,176,171 B2 | 2/2007 | Nieendick et al. |
| 9,890,107 B2 | 2/2018 | Schuch et al. |
| 10,370,493 B2 | 8/2019 | Brandt et al. |
| 10,618,867 B2 | 4/2020 | Liebig et al. |
| 2005/0158270 A1 | 7/2005 | Frantz et al. |
| 2015/0297485 A1 | 10/2015 | Kleinen et al. |
| 2018/0110718 A1* | 4/2018 | Hloucha ............... A61K 8/922 |
| 2018/0133133 A1 | 5/2018 | Kleinen et al. |
| 2018/0344602 A1 | 12/2018 | Schuch et al. |
| 2020/0155436 A1 | 5/2020 | Hartung et al. |
| 2021/0154115 A1 | 5/2021 | Schwab et al. |

FOREIGN PATENT DOCUMENTS

| | | |
|---|---|---|
| CN | 111971023 | 11/2020 |
| DE | 19801231 C1 | 4/1999 |
| EP | 0568848 A1 | 11/1993 |
| EP | 2 932 960 A1 | 10/2015 |
| JP | 2003055165 | 2/2003 |
| JP | 2003055165 A * | 2/2003 |
| WO | 1994024248 | 10/1994 |
| WO | 02/05781 A1 | 1/2002 |

OTHER PUBLICATIONS

Brandt et al., U.S. Appl. No. 16/857,523, filed Apr. 24, 2020.
European Search Report dated Mar. 19, 2020 in EP 19195481.7 (8 pages).

* cited by examiner

*Primary Examiner* — Snigdha Maewall
(74) *Attorney, Agent, or Firm* — Grüneberg and Myers PLLC

(57) ABSTRACT

The invention relates to a process for preparing an opaque composition using ethylene glycol distearate.

9 Claims, 1 Drawing Sheet

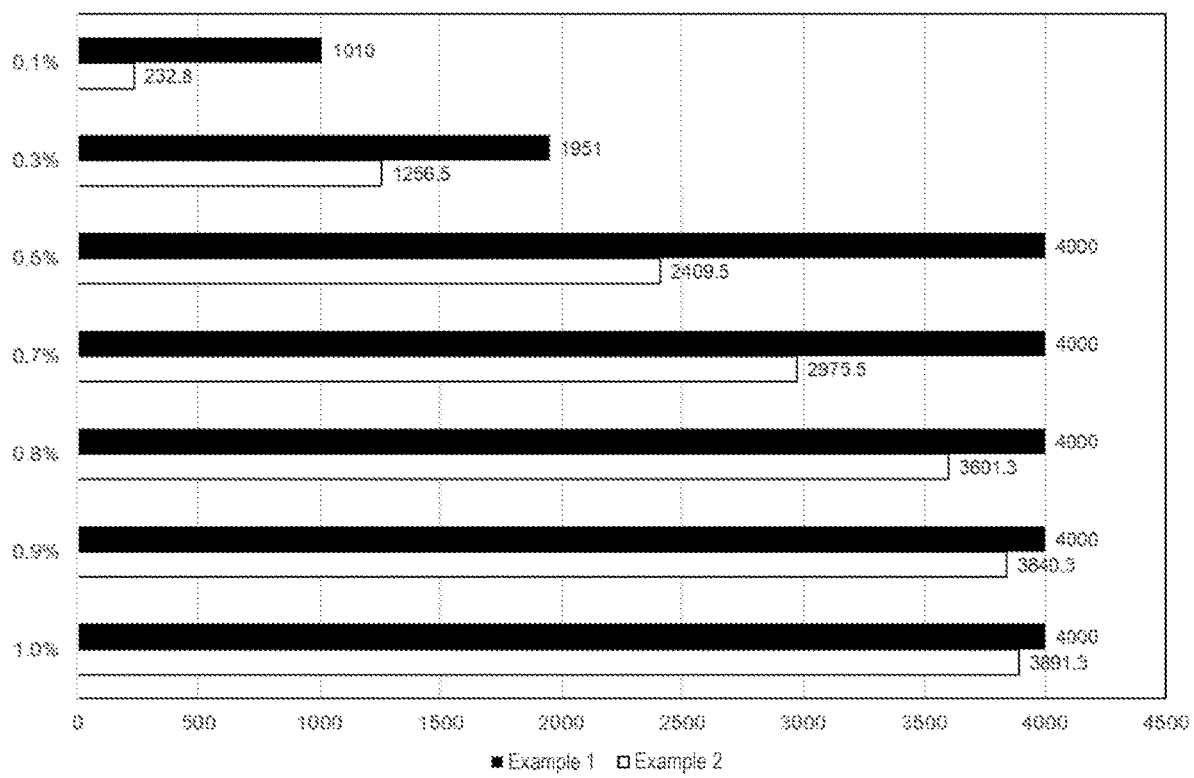

OPAQUE COMPOSITION COMPRISING ETHYLENE GLYCOL DISTEARATE

CROSS REFERENCE TO RELATED APPLICATIONS

This application is a 35 U.S.C. § 119 patent application which claims the benefit of European Application No. 19195481.7 filed Sep. 5, 2019, which is incorporated herein by reference in its entirety.

FIELD

The invention relates to a process for preparing an opaque composition using ethylene glycol distearate.

BACKGROUND

Ethylene glycol distearate (EGDS) has long been used for achieving pearlescent effects in formulations. For cosmetic formulations, this pearlizer is sold under the INCI name glycol distearate for example.

For instance, CN192816613 describes the preparation of pearlescent ethylene glycol distearate in an aqueous medium with a surface-active substance with heating and cooling and subsequent pH adjustment. The pearlescent ethylene glycol distearate is also used in low-water-content car wash formulations.

JP2003055165 discloses opacifiers composed of fatty acid glycol esters and emulsifiers and also surfactants.

DE19801231 discloses a process for producing free-flowing pearlescent and opacifier concentrates, in which an emulsifier-containing aqueous wax body premix is produced in a first reactor and this is sprayed into a second reactor filled with an aqueous surfactant solution.

WO1994024248 discloses a pearlizing agent for such products as shampoos and hand soaps, that contains a glycol distearate, an alkyl polyglycoside, a certain betaine, a glycol, and water.

US20050158270 discloses an aqueous pearlizing concentrate, comprising a pearlizing agent, an anionic surfactant, and a cationic component.

EP0568848 discloses flowable aqueous pearlescent dispersions with fatty acid glycol esters as pearlescent agents.

Common to all processes of the prior art is that they must always be operated with a combination of emulsifier and surfactant.

SUMMARY

Due to the ongoing discussion about microplastics in cosmetic products, manufacturers are looking for alternatives to the styrene-acrylate copolymers (styrene/acrylates copolymer) used as opacifier.

The object of the invention was to provide a simplified production process for opacifers.

DETAILED DESCRIPTION

Surprisingly, it has now been found that exceptional opacifiers can also be produced even completely without the use of an emulsifier component.

The present invention therefore provides a process for preparing a composition comprising ethylene glycol distearate as described in claim 1.

The invention further provides certain opaque compositions comprising ethylene glycol distearate which may be used as opacifiers, and also opaque formulations comprising the opaque compositions according to the invention.

An advantage of the present invention is that the opaque compositions, at comparable use concentration in formulations, produce a comparable whiteness and a comparable, preferably improved, turbidity value in relation to the conventional styrene-acrylate copolymers.

A further advantage of the present invention is that the opaque compositions are not highly viscous and therefore can be easily pumped. The liquid state of matter is an important property, particularly for the continuous production of surfactant formulations. Owing to the liquid form, the manufacturer can process the concentrate cold and there is in turn no risk of triggering crystallization to an undesirable crystal structure by an otherwise necessary melt process.

Another advantage of the present invention is that the constituents of the composition are readily biodegradable.

A further advantage of the present invention is that the composition, in a particular embodiment, is free of polyethylene glycol constituents.

A further advantage of the present invention is the high degree of whiteness of the opacifiers.

A further advantage of the present invention is that the degree of whiteness does not change on storage.

Another advantage of the present invention is the low particle size of the opacifiers.

A further advantage of the present invention is the low abrasion effect of the opacifiers associated with a good soft skin feel.

A further advantage of the present invention is the good compatibility of the opacifiers with other formulation components, which prevents agglomeration.

Another advantage of the present invention is the good dispersibility of the opacifiers.

A further advantage of the present invention is the low solubility of the opacifiers in many solvents, particularly in formulations suitable for cosmetic purposes.

Yet another advantage of the present invention is the outstanding opacity, measured by fineness and refractive index of the opacifiers.

In the present case, therefore, what is claimed is a process for preparing an opaque composition, which preferably has no pearlescence, comprising the steps of
  a) providing a starting composition comprising
    A) 1.0% by weight to 20.0% by weight, preferably 5.0% by weight to 20.0% by weight of at least one surfactant,
    B) 5.0% by weight to 30.0% by weight ethylene glycol distearate,
    C) 20.0% by weight to 89.0% by weight, preferably 20.0% by weight to 85.0% by weight water, wherein the percentages by weight refer to the total starting composition,
  b) stirring the starting composition at a temperature in a range from 60° C. to 100° C., preferably 65° C. to 95° C. and particularly preferably 70° C. to 90° C.,
  c) cooling to a temperature in a range from 5° C. to 55° C., preferably 10° C. to 50° C., particularly preferably 15° C. to 45° C. to obtain the opaque composition,
  characterized in that the total surfactant amount accounts for at least 90% by weight, preferably at least 95% by weight, particularly preferably at least 98% by weight, based on the amount of all surface-active substances present in the starting composition.

Preferably the stirring in process step b) according to the instant invention is conducted at a rotational speed of 100 rpm-25000 rpm, preferably 1000 rpm-20000 rpm, particularly preferably at 2000 rpm-15000 rpm.

In contrast to transparent materials are materials referred to as translucent or transparent, which allow light to pass through but behind which, as in the case of frosted glass, no items are recognizable. In the case of materials impervious to light, in contrast, this is referred to as opacity. Opacity is a measure of the opaqueness (turbidity) of substances and is the reciprocal of translucence. Opacity is the reciprocal of transmission.

In the context of the present invention, the term "opaque" is consequently understood to mean compositions which are cloudy to a certain degree.

The cloudiness, also turbidity (lat. turbidus, 'cloudy'), of a liquid is caused by small particles which have a refractive index different from the carrier substance or cause absorption. Nowadays, the turbidity of a liquid is determined optically and measured by means of electronic evaluation. The wavelength of the measuring radiation is typically in the infrared region at 860 nm (according to ISO 7027).

Generally two measuring methods are distinguished:

attenuation of the light radiation passing through (transmitted light), most suitable for detection of relatively dense turbidity.

Sideways scattering of the light radiation (scattered light), most suitable for detection of weak turbidity.

In order to be able to measure turbidity in a manner that allows comparison, the turbidity standard liquid formazine was created. All turbidity units refer to dilutions of this liquid. The most commonly used turbidity units are:

FAU Formazine Attenuation Units—measurement of transmitted light (angle 0°) according to the specifications of the standard ISO 7027

FNU Formazine Nephelometric Units—measurement of scattered light (angle 90°) according to the specifications of the standard ISO 7027

FTU Formazine Turbidity Unit—the unit used in water treatment

In the context of the present invention, the term "opaque" is consequently understood to mean compositions having a turbidity value of 500 Formazine Nephelometric Units or more. The Formazine Nephelometric Units abbreviated as FNU in the context of the present invention are determined by a scattered light measurement, such as conducted in the examples of the present document.

In the context of the present invention, the term "having no pearlescence" or "having no pearlescence properties" is understood to mean that the opaque composition according to the invention under consideration has a luminance of greater than or equal to 187 as a 3 percent by weight low-viscosity aqueous composition, wherein the percentages by weight refer to the total aqueous composition. Such high luminance values cannot be attained by pearlescent compositions owing to the occurrence of light scattering.

In the context of the present invention, the luminance is determined as carried out in the examples of the present document.

In the context of the present invention, the term "surface-active substances" is understood to mean substances with interface-active properties which have the ability to reduce the surface tension of water at 20° C. and at a concentration of 0.5% by weight, based on the total composition, to below 45 mN/m.

The surface tension is determined by the ring method in accordance with du Noüy at 20° C.

In the context of the present invention, the term "surfactant" is understood to mean substances with interface-active properties.

In the context of the present invention, the terms "surfactant" and "emulsifier" are understood to mean organic substances with interface-active properties which have the ability to reduce the surface tension of water at 20° C. and at a concentration of 0.5% by weight, based on the total composition, to below 45 mN/m. In this case, considered in a pH range of 2 to 12 and at a temperature of 20° C., surfactants have positively and/or negatively charged functional groups in their chemical structural formula, whereas emulsifiers contain no charged functional groups with respect to their chemical structural formula.

The surface tension is determined by the ring method in accordance with du Noüy at 20° C.

As a consequence, in the context of the present invention, emulsifiers and surfactants can be clearly distinguished from each other and do not overlap.

The "pH" in connection with the present invention is defined as the value which is measured for the relevant composition at 20° C. after stirring for five minutes using a pH electrode calibrated in accordance with ISO 4319 (1977).

Unless stated otherwise, all percentages (%) given are percentages by mass.

A process preferred according to the invention is characterized in that at least two surfactants are present in component A).

The at least one surfactant in component A) is in accordance with the invention preferably selected from the group consisting of cationic, anionic and amphoteric surfactants comprising at least one nitrogen atom or one sulphur atom, particularly trialkylammonium salts, amino acid esters, amphoacetates, amphodiacetates, amphopropionates, betaines, sultaines, sulphosuccinates, glutamates, glycinates, sarcosinates, carboxylates, sulphonates, isethionates and sulphates.

The sulphosuccinates, which may optionally be alkoxylated, particularly optionally ethoxylated, are in accordance with the invention particularly preferably monoester-derived sulphosuccinates, especially disodium laureth sulphosuccinates and disodium lauryl sulphosuccinates.

Sulphate preferred in accordance with the invention is selected from sodium lauryl sulphate (Sodium Lauryl Sulphate, SLS) and sodium lauryl ether sulphate, also known as Sodium Laureth Sulphate (SLES), preferably sodium lauryl ether sulphate.

Betaines preferred in accordance with the invention are alkyl and amidopropyl betaines, especially cocamidopropyl betaine (CAPB).

It is particularly of advantage if, in the process of the present invention, component A) is a mixture of sodium laureth sulphate and cocamidopropyl betaine or a mixture of sodium lauryl sulphate and cocamidopropyl betaine, especially in a ratio by weight of sulphate to betaine from 15:1 to 1:2.

In a preferred embodiment, the process according to the invention is one for preparing an opaque composition which is essentially free of polyethers and compounds comprising polyethers and preferably has no pearlescence.

Therefore, all components used in this preferred embodiment of the process according to the invention are essentially free of polyethers and compounds comprising polyethers.

In the context of the present invention, the term "essentially free of polyethers and compounds comprising polyethers" describes the fact that compounds present comprise only traces of, and preferably do not comprise, any alkoxy groups, oligoalkoxy groups or polyalkoxy groups such as ethylene oxide or propylene oxide for example. The concentration of compounds comprising polyethers should be less than 0.1% by weight, particularly preferably less than 0.01% by weight, based on the total formulation, preferably below the detection limit of customary analytical methods such as GC, HPLC, NMR spectroscopy, GPC or MALDI.

In this preferred embodiment of the process according to the invention, component A) preferably used is selected from sulphosuccinates, preferably monoester-derived sulphosuccinates, such as disodium lauryl sulphosuccinate, disodium undecylenamido MEA sulphosuccinate, disodium ricinoleamido MEA sulphosuccinate, diethylhexyl sodium sulphosuccinate, disodium cocamide MEA sulphosuccinate, ammonium dinonyl sulphosuccinate, ammonium lauryl sulphosuccinate, diammonium lauramido MEA sulphosuccinate, diammonium lauryl sulphosuccinate, diamyl sodium sulphosuccinate, dicapryl sodium sulphosuccinate, dicyclohexyl sodium sulphosuccinate, diheptyl sodium sulphosuccinate, dihexyl sodium sulphosuccinate, diisobutyl sodium sulphosuccinate, dioctyl sodium sulphosuccinate, disodium cetearyl sulphosuccinate, disodium cocamide MEA-sulphosuccinate, disodium cocamide MIPA-sulphosuccinate, disodium coco-glucoside sulphosuccinate, disodium dihydroxyethyl sulphosuccinyl undecilenate, disodium hydrogenated cottonseed glyceride sulphosuccinate, disodium isodecyl sulphosuccinate, disodium isostearamido MEA-sulphosuccinate, disodium isostearamido MIPA-sulphosuccinate, disodium isostearyl sulphosuccinate, disodium lauramido MEA-sulphosuccinate, disodium myristamido MEA-sulphosuccinate, disodium oleamido MEA sulphosuccinate, disodium oleamido MIPA sulphosuccinate, disodium oleyl sulphosuccinate, disodium ricinoleamido MEA-sulphosuccinate, disodium stearamido MEA-sulphosuccinate, disodium stearyl sulfosuccinamate, disodium stearyl sulphosuccinate, disodium tallamido MEA-sulphosuccinate, disodium tallowamido MEA-sulphosuccinate, disodium tallow sulfosuccinamate, disodium tridecyl sulphosuccinate, disodium wheat germamido MEA-sulphosuccinate, ditridecyl sodium sulphosuccinate, sodium bisglycol ricinosulphosuccinate As component B) it is also possible to use technical grade ethylene glycol distearate as the ethylene glycol distearate, the degree of esterification of which for example is not exactly two ("diester"), but for example is 1.5 (so-called "ethylene glycol sesquistearate"). In addition or as an alternative, for example, some of the stearic acid residues may be substituted by palmitic acid residues.

It is preferable in accordance with the invention that the starting composition of process step a) has a pH of 4 to 7 at 20° C.

It is preferable in accordance with the invention that the stirring in process step b) has a duration of 0.25 to 6.0 hours, preferably 0.5 to 4.0 hours.

A process preferred according to the invention is characterized in that components A) to C) of the starting composition are in the form of a homogeneous emulsion in process step b).

Process step c) of the process according to the invention is preferably carried out at a cooling rate of 0.1° C./min to 15° C./min, preferably 0.2° C./min to 10° C./min, particularly preferably 0.3° C./min to 5° C./min.

In process steps b) and/or c), it is possible to add additionally component D), water, preferably up to a maximum concentration of 85% by weight, based on the opaque composition.

A process preferred according to the invention is characterized in that in process step c) the cooling is carried out partially by adding water, the water preferably having a temperature of from 4° C. to 25° C., more preferably 8° C.

to 21XXX ° C., to the starting composition, preferably obtaining an opaque composition having a water content of 50% by weight to 85% by weight water, where the percentages by weight refer to the total composition.

The present invention further provides an opaque composition obtainable by the process according to the invention.

The present invention still further provides an opaque composition comprising

A2) 1.0% by weight to 25.0% by weight, preferably 5.0% by weight to 20.0% by weight of at least one surfactant, B2) 5.0% by weight to 30.0% by weight ethylene glycol distearate, C2) 20.0% by weight to 89.0% by weight, preferably 20.0% by weight to 85.0% by weight water, where the percentages by weight refer to the total composition, characterized in that the total surfactant amount accounts for at least 90% by weight, preferably at least 95% by weight, particularly preferably at least 98% by weight, based on the amount of all surface-active substances present in the composition.

In accordance with the invention, the compositions according to the invention preferably comprise components A2), B2 and C2) in sum total to an extent of at least 66% by weight, preferably at least 90% by weight, based on the total composition.

The opaque compositions obtainable by the process according to the invention and the compositions according to the invention preferably have a viscosity of 10 to 30 000 mPa s, particularly preferably a viscosity of 100 to 10 000 mPa s, especially preferably a viscosity of 500 to 7000 mPa s, measured at 25° C. with a Brookfield viscometer using RV spindle=5 and at 10 rpm.

The opaque compositions obtainable by the process according to the invention and the opaque compositions according to the invention, at a concentration of 0.3% by weight in water, where the percentages by weight refer to the sum total of water and total composition, preferably have a turbidity value of 500, preferably 1000, particularly preferably 1200, especially preferably 1500 or more formazine nephelometric units.

The opaque compositions obtainable by the process according to the invention and the opaque compositions according to the invention differ from those of the prior art in particular in that they have no pearlescent properties.

The opaque compositions obtainable by the process according to the invention and the opaque compositions according to the invention, as a 3 percent by weight low-viscosity aqueous composition, wherein the percentages by weight refer to the total aqueous composition, preferably have a luminance of greater than 187, preferably greater than 190.

Components A2), B2) and C2) are preferably weighted according to the preference for the respective components A), B) and C) of the process according to the invention; the same applies accordingly to the preferred combinations of the components.

The opaque compositions obtainable by the process according to the invention and the opaque compositions according to the invention are therefore also preferably essentially free of polyethers and compounds comprising polyethers.

The opaque compositions obtainable by the process according to the invention and the opaque compositions according to the invention are outstandingly suitable for preparing opaque formulations, particularly cosmetic formulations, very particularly cleansing formulations for skin and/or hair.

These opaque compositions according to the invention can be prepared in a further process according to the invention for preparing opaque formulations, particularly opaque cosmetic formulations, very particularly opaque cleansing formulations for skin and/or hair, which comprises the process steps of:

a) providing a starting composition comprising
   A) 1.0% by weight to 25.0% by weight of at least one surfactant,
   B) 5.0% by weight to 30.0% by weight ethylene glycol distearate,
   C) 20.0% by weight to 89.0% by weight water,
      wherein the percentages by weight refer to the total starting composition,
b) stirring the starting composition at a temperature in a range from 60° C. to 100° C., preferably 65° C. to 95° C. and particularly preferably 70° C. to 90° C.,
c) cooling to a temperature in a range from 5° C. to 55° C., preferably 10° C. to 50° C., particularly preferably 15° C. to 45° C. to obtain the opaque composition,
d) blending the opaque composition with further components in a temperature range from 5° C. to 40° C., preferably 10° C. to 35° C., particularly preferably 15° C. to 25° C., to obtain an opaque formulation,
characterized in that the total surfactant amount accounts for at least 90% by weight, preferably at least 95% by weight, particularly preferably at least 98% by weight, based on the amount of all surface-active substances present in the starting composition.

In this further process according to the invention, the identical preferred embodiments are used in process step a) to c) as described above for the first process according to the invention.

It is preferred in this further process according to the invention that components A), B) and C) in sum total constitute at least 0.5% by weight, based on the formulation obtained by this further process according to the invention.

The present invention therefore further provides also opaque formulations comprising opaque compositions obtainable by the first process according to the invention and/or compositions according to the invention, preferably in an amount of 0.1% by weight to 15% by weight, particularly preferably 0.5% by weight to 10% by weight, especially preferably 1% by weight to 6% by weight, where the percentages by weight refer to the total formulation.

The opaque formulations according to the invention preferably have a turbidity value of 600, preferably 750, particularly 1000, especially preferably 1200 or more formazine nephelometric units.

The opaque formulations according to the invention are preferably characterized in that they have no pearlescent properties.

The present invention further relates to the use of opaque compositions obtainable by the first process according to the invention and/or the opaque compositions according to the invention as opacifiers, particularly without a pearlescent effect being generated in the use according to the invention.

The examples which follow describe the present invention by way of example, without any intention of restricting the invention, the scope of which is apparent from the entirety of the description and the claims, to the embodiments recited in the examples.

BRIEF DESCRIPTION OF THE DRAWING

The FIG. shows turbidity values.

EXAMPLES

Example 1 (Inventive)

A mixture consisting of 3.6% by weight cocamidopropyl betaine (38% active), 21.1% by weight sodium lauryl ether sulphate (28%), 17% by weight glycol distearate, 0.5% sodium benzoate and 57.8% by weight water was stirred at 80° C. for 1 h. The mixture was then homogenized using an Ultra-Turrax for 2 minutes at 12 000 revolutions per minute. With constant stirring, the mixture was cooled to 23° C. over a period of 60 minutes.

A white homogeneous suspension was obtained, which was stored at 22° C. and which had a viscosity of 445 mPa s after 24 h and 655 mPa s after 1 week. The suspension exhibited no separation effects over 6, and neither over 10, weeks.

Example 1b (Inventive)

A mixture of 58.6 parts by weight of 26 wt.-% aqueous disodium laureth sulphate, 15 parts by weight ethylene glycol distearate and 26.4 parts by weight water were mixed and heated to 80° C. The mixture was then homogenized using an Ultra-Turrax for 2 minutes at 12 000 revolutions per minute. With constant stirring, the mixture was cooled to 22° C. over a period of 20 minutes. A white homogeneous suspension was obtained, which was stored at 22° C. and which had a viscosity of 302 mPa s after 24 h and 554 mPa s after 1 week. The suspension exhibited no separation effects over 10 weeks.

Example 2 (Non-Inventive)

A mixture of 5 parts by weight disodium laureth sulphosuccinate, 7 parts by weight laureth-4, 17 parts by weight glycol distearate and 25 parts by weight water was stirred at 80° C. for 0.5 h. The mixture was then cooled to 35° C. over 20 minutes by adding 45 parts by weight water (20° C.). A white homogeneous suspension was obtained, which was stored at 22° C. and which had a viscosity of 340 mPa s after 24 h and 452 mPa s after 1 week. The suspension exhibited no separation effects over 6 weeks.

Example 2b (Non-Inventive)

A mixture of 58.6 parts by weight of 26 wt.-% aqueous disodium laureth sulphate, 15 parts by weight ethylene glycol distearate and 26.4 parts by weight water were mixed and heated to 80° C. The mixture was then homogenized using an Ultra-Turrax for 2 minutes at 12 000 revolutions per minute. With constant stirring, the mixture was cooled to 25° C. over a period of 660 minutes. A white homogeneous suspension was obtained, which was stored at 22° C. and which had a viscosity of 553 mPa s after 24 h and 750 mPa s after 1 week. The suspension exhibited no separation effects over 10 weeks.

The product showed a strong pearlizing effect.

Example 3: Determination of the Pearlescent Properties

To determine the luminance, 3% of the blend is thoroughly stirred into a surfactant mixture composed of SLES/

CAPB (11.2:3.8 active matter), which has been thickened with 0.8% PEG-18 glyceryl oleate/cocoate (ANTIL 171, distributed commercially by EVONIK Nutrition&Care GmbH) and ca. 0.4% NaCl, such that a viscosity of 3000-4000 mPas (Brookfield, spindle 2, 30 rpm) is achieved.

38 g of these formulations are then filled into a black lid composed of plastic (height 1.9 cm; diameter 5.9 cm) and placed on a black background, which is in a light tent (manufacturer Neewer, product number 10026118, size 40×40×40 cm). A digital camera (Canon EOS 605) equipped with a zoom lens (Canon EF-S 18-55 mm, 1:3.5-5.6) is fixed 32 cm above the upper edge of the lid. For uniform illumination of the sample, an external light source (eSmart ESL Photolamp: E27, diameter 72 mm, length 235 mm, 50 W, 3200 lumens, 5500K) is positioned right and left respectively of the light tent. The photos are taken at an aperture of f/5.5 and an exposure time of $\frac{1}{100}$s, and 55 mm zoom setting. To analyze the photos, the photoshop CC 2015 version 2015.0.1 program is used. For this purpose, a 60×60 mm large image section is cropped from the middle of the photo and the histogram read out. The values for the luminance thus obtained are evaluated and compared.

The pearlizing agent TEGO Pearl N 300, distributed commercially by EVONIK Nutrition&Care GmbH, serves as comparative substance.

| | |
|---|---|
| Example 1 (inventive) | 193 |
| Example 1b (inventive) | 194 |
| Example 2 (non-inventive) | 190 |
| Example 2b (non-inventive) | 179 |
| TEGO Pearl N 300 (comparison) | 180 |

Example 4: Determination of the Turbidity Values of Formulations According to the Invention Comprising Inventive Opaque Composition The inventive composition of example 1 was homogeneously stirred into a surfactant mixture consisting of 9 parts by weight SLES (Sodium Laureth Sulphate) and 3 parts by weight CAPB (Cocamidopropyl Betaine) according to Table 1 and thickened by adding 1% NaCl:

TABLE 1

Inventive opaque formulations 1-7 prepared from inventive example 1

| | 1 | 2 | 3 | 4 | 5 | 6 | 7 |
|---|---|---|---|---|---|---|---|
| SLES (28% a.m.) | 32 | 32 | 32 | 32 | 32 | 32 | 32 |
| Water | 58.65 | 58.45 | 58.25 | 58.05 | 57.95 | 57.85 | 57.75 |
| TEGO ® Betain F 50 (38% a.m.) | 8 | 8 | 8 | 8 | 8 | 8 | 8 |
| Inventive Example 1 | 0.1 | 0.3 | 0.5 | 0.7 | 0.8 | 0.9 | 1 |
| NaCl | 0.8 | 0.8 | 0.8 | 0.8 | 0.8 | 0.8 | 0.8 |
| Neolone PE | 0.45 | 0.45 | 0.45 | 0.45 | 0.45 | 0.45 | 0.45 |
| pH | 5.5 | 5.5 | 5.5 | 5.5 | 5.5 | 5.5 | 5.5 |

For comparison, comparative example 2 was also stirred homogeneously into the same surfactant mixture and analogously thickened:

TABLE 2

Comparative formulations C1-C7

| | C1 | C2 | C3 | C4 | C5 | C6 | C7 |
|---|---|---|---|---|---|---|---|
| SLES (28% a.m.) | 32 | 32 | 32 | 32 | 32 | 32 | 32 |
| Water | 58.65 | 58.45 | 58.25 | 58.05 | 57.95 | 57.85 | 57.75 |
| TEGO ® Betain F 50 (38% a.m.) | 8 | 8 | 8 | 8 | 8 | 8 | 8 |
| Comparative example 2 | 0.1 | 0.3 | 0.5 | 0.7 | 0.8 | 0.9 | 1 |
| NaCl | 0.8 | 0.8 | 0.8 | 0.8 | 0.8 | 0.8 | 0.8 |
| Neolone PE | 0.45 | 0.45 | 0.45 | 0.45 | 0.45 | 0.45 | 0.45 |
| pH | 5.5 | 5.5 | 5.5 | 5.5 | 5.5 | 5.5 | 5.5 |

The turbidity values were determined for the inventive opaque formulations 1-7 and the comparative formulations C1-C7.

The measuring instrument used was an Iso Turbidity Meter, HI 88713 from Hanna Instruments, which was operated in the measuring mode: "NTU ratio mode". For this purpose, indexed cuvettes were filled up to the 10 ml mark and degassed. The cuvettes were then measured in the measurement cell at room temperature. The cuvette was turned 90° after each measurement. In this way, four measurements in total were taken and the average value then calculated. The measured values are reported in NTU.

The results are shown in the FIGURE. The measured values in the FIGURE show that the formulations according to the invention have significantly higher turbidity values at the same active content, particularly even at low use concentrations.

The invention claimed is:

1. A process for preparing an opaque composition, comprising the steps of:
    a) providing a starting composition comprising
        A) from 1.0% by weight to 25.0% by weight of at least one surfactant,
        B) from 5.0% by weight to 30.0% by weight ethylene glycol distearate,
        C) from 20.0% by weight to 89.0% by weight water,
        wherein the percentages by weight refer to the total starting composition,
    b) stirring the starting composition at a temperature in a range from 60° C. to 100° C.,
    c) cooling to a temperature in a range from 5° C. to 55° C. to obtain the opaque composition wherein the cooling is carried out by adding water to the starting composition, obtaining an opaque composition having a water content of from 50% by weight to 85% by weight water, where the percentages by weight refer to the total composition,
    wherein the total surfactant amount accounts for at least 90% by weight based on the amount of all surface-active substances present in the starting composition,
    wherein at least two surfactants are present in component A), and
    said at least one surfactant is an organic substance with interface-active properties which have the ability to reduce the surface tension of water at 20° C. and at a concentration of 0.5% by weight, based on the total composition, to below 45 mN/m and
    considered in a pH range of 2 to 12 and at a temperature of 20° C., said at least one surfactant has positively and/or negatively charged functional groups in its chemical structural formula, and wherein said opaque composition has a turbidity of at least 600 nephelometric units.

2. The process according to claim 1, wherein the at least one surfactant in component A) is selected from the group consisting of anionic and amphoteric surfactants comprising at least one nitrogen atom or one sulphur atom, amphoacetates, amphopropionates, betaines, sulphosuccinates and sulphates.

3. The process according to claim 1, wherein the starting composition of process step a) has a pH of from 4 to 7 at 20° C.

4. The process according to claim 1, wherein process step c) is carried out at a cooling rate of 0.1° C./min to 15° C./min.

5. The process according to claim 1, wherein in step c) the cooling is carried out at a cooling rate of 0.3° C./min to 5° C./min.

6. A process for preparing opaque formulations, comprising the process steps of
   a) providing a starting composition comprising
      A) from 5.0% by weight to 20.0% by weight of at least one surfactant,
      B) from 5.0% by weight to 30.0% by weight ethylene glycol distearate,
      C) from 20.0% by weight to 85.0% by weight water,
      wherein the percentages by weight refer to the total starting composition,
   b) stirring the starting composition at a temperature in a range from 60° C. to 100° C.,
   c) cooling to a temperature in a range from 5° C. to 55° C. to obtain the opaque composition,
   d) blending the opaque composition obtained according to the process of claim 1 with further components in a temperature range from 5° C. to 40° C. to obtain an opaque formulation,
   wherein the total surfactant amount accounts for at least 90% by weight based on the amount of all surface-active substances present in the starting composition,
   wherein at least two surfactants are present in component A), and
   said at least one surfactant is an organic substance with interface-active properties which have the ability to reduce the surface tension of water at 20° C. and at a concentration of 0.5% by weight, based on the total composition, to below 45 mN/m and
   considered in a pH range of 2 to 12 and at a temperature of 20° C., said at least one surfactant has positively and/or negatively charged functional groups in its chemical structural formula.

7. The process according to claim 1, wherein
   b) stirring the starting composition at a temperature in a range from 70° C. to 90° C.,
   c) cooling to a temperature in a range from 15° C. to 45° C. to obtain the opaque composition,
   wherein the total surfactant amount accounts for at least 95% by weight based on the amount of all surface-active substances present in the starting composition.

8. The process according to claim 1, wherein process step c) is carried out at a cooling rate of from 0.2° C./min to 10° C./min.

9. The process according to claim 6, wherein
   b) stirring the starting composition at a temperature in a range from 70° C. to 90° C.,
   c) cooling to a temperature in a range from 15° C. to 45° C. to obtain the opaque composition,
   d) blending the opaque composition with further components in a temperature range from 15° C. to 25° C. to obtain an opaque formulation,
   wherein the total surfactant amount accounts for at least 98% by weight based on the amount of all surface-active substances present in the starting composition.

* * * * *